United States Patent [19]

Goodman et al.

[11] 4,416,145

[45] Nov. 22, 1983

[54] ULTRASONIC LEAK DETECTING METHOD AND APPARATUS

[75] Inventors: Mark Goodman; John R. Zeno, both of New York; Marty Borruso, Brooklyn, all of N.Y.

[73] Assignee: UE Systems, Inc., New York, N.Y.

[21] Appl. No.: 347,584

[22] Filed: Feb. 10, 1982

[51] Int. Cl.³ ............................................. G01N 29/04
[52] U.S. Cl. ................................. 73/40.5 A; 73/592; 73/632; 73/658
[58] Field of Search ...................... 73/40, 40.5 A, 45.5, 73/592, 591, 593, 620, 632, 658; 367/137; 310/334, 335, 336; 331/116 R

[56] References Cited

U.S. PATENT DOCUMENTS

| | | | |
|---|---|---|---|
| 2,665,257 | 1/1954 | Potter | 73/40 |
| 3,222,635 | 12/1965 | Simpkins et al. | 73/592 |
| 3,374,663 | 3/1968 | Morris | 73/654 |
| 3,592,967 | 7/1971 | Harris | 73/40.5 A |
| 3,978,915 | 9/1976 | Harris | 73/592 |

Primary Examiner—Stephen A. Kreitman
Attorney, Agent, or Firm—Darby & Darby

[57] ABSTRACT

Leaks or thin spots in containers, as well as mechanical faults, e.g. worn bearings, are detected by an ultrasonic energy indicator that includes a modulator that heterodynes ultrasonic signals received by a transducer and creates an audio signal related thereto. The transducer includes a series arrangement of piezoelectric crystals feeding a field-effect transistor amplifier and the modulator operates in an amplitude modulation, suppressed-carrier mode which can be stabilized by a feedback loop. For indicating the presence of the audio signal, either headphones or a meter or both are employed. When leaks in a container are being detected, an ultrasonic generator is used which varies its output frequency slowly over a band of frequencies. The leak detection technique can be improved by applying a thin layer of a liquid to the container surface so that pressure introduced into the container causes the formation and bursting of bubbles in the liquid that results in the production of ultrasonic energy.

31 Claims, 3 Drawing Figures

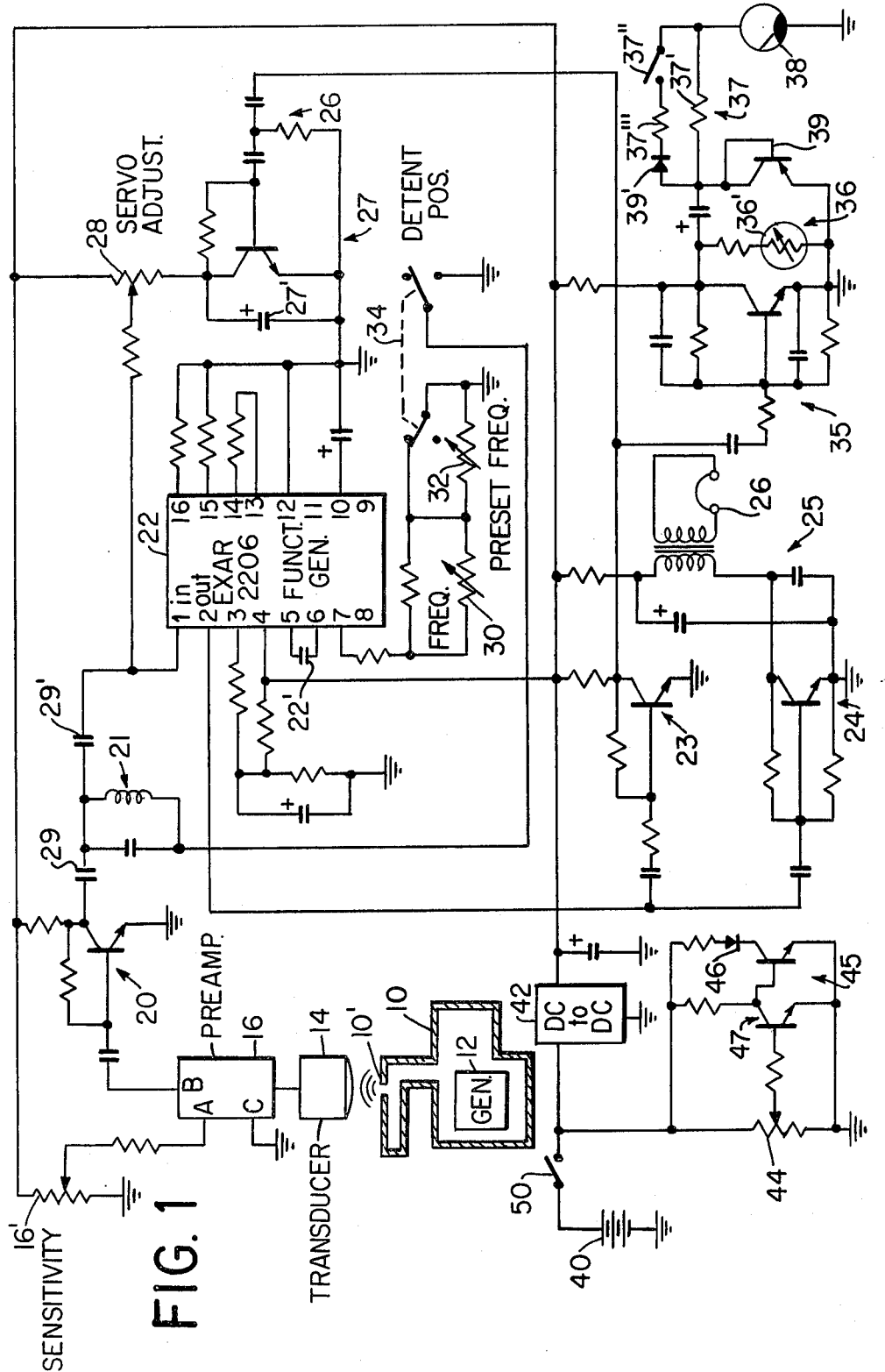

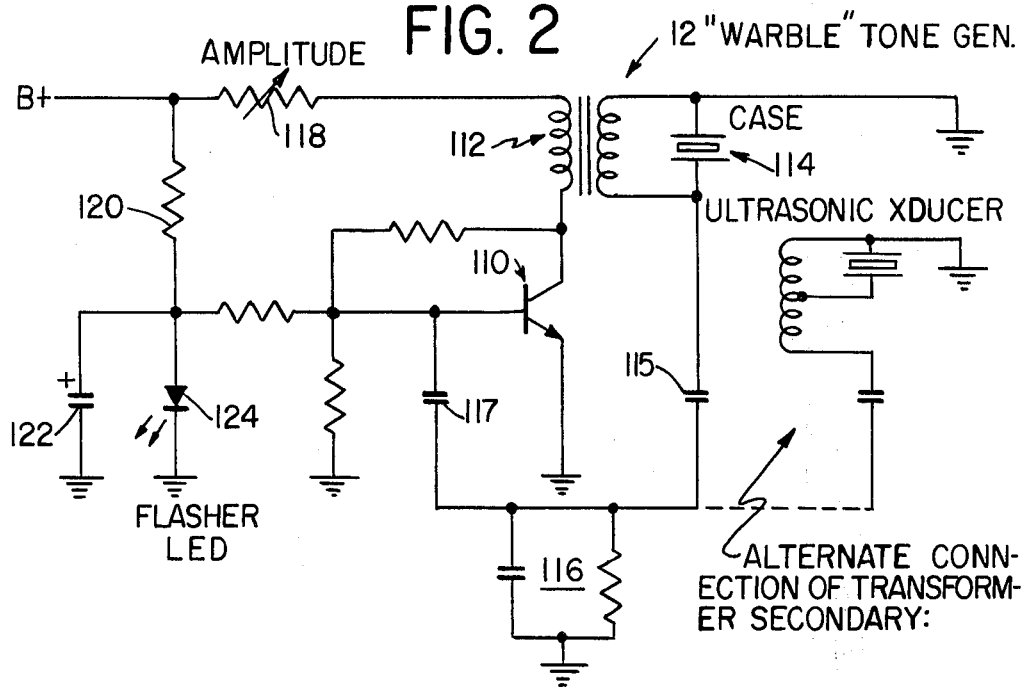
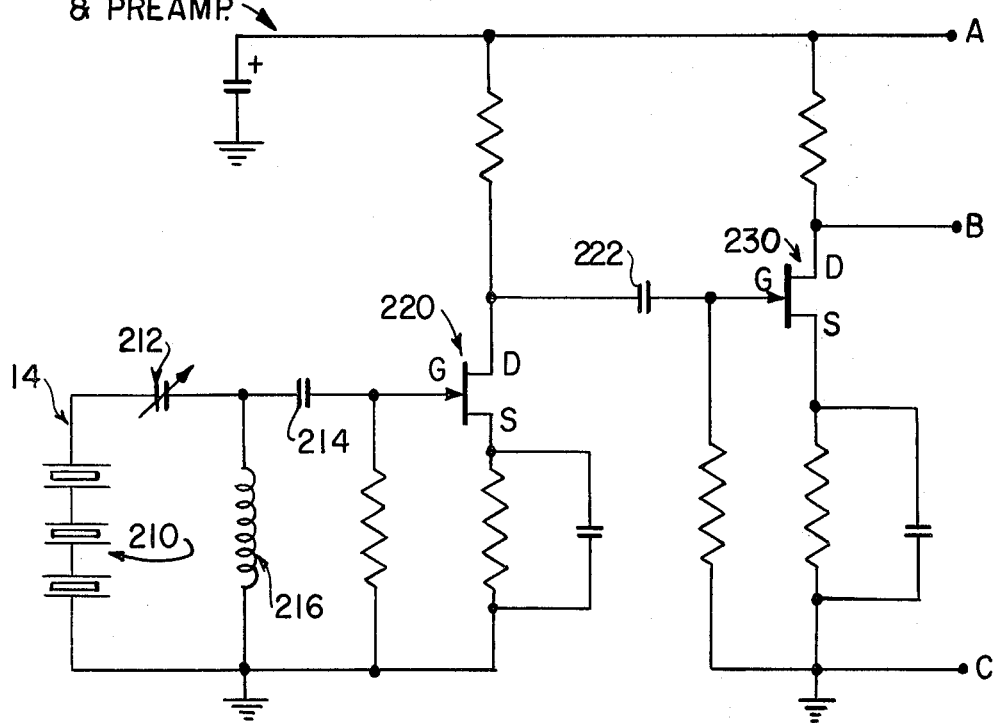

ULTRASONIC LEAK DETECTING METHOD AND APPARATUS

BACKGROUND OF THE DISCLOSURE

This invention relates to ultrasonic apparatus and more particularly, to methods and apparatus for detecting leaks and malfunctions of mechanical parts by ultrasonic means.

It is well known that ultrasonic generators and detectors can be used to locate leaks, e.g. in pipes. Such a system is shown in U.S. Pat. No. 3,978,915 to Harris. In that arrangement ultrasonic generators are positioned in a chamber through which the pipes pass. At the ends of these pipes, exterior to the chamber, ultrasonic detectors are located. At the point where a leak occurs in the pipe or the pipe wall is thin, the ultrasonic energy will enter the pipe and travel along the pipe to the end where the detector resides. Thus the detector will receive a signal indicating the existance of this leak or weak spot. Since ultrasonic energy used for such purposes is generally in the range of 40 KHz, it is too high in frequency to be heard by a human being. Thus, means are provided for heterodyning or frequency shifting the detected signal into the audio range and various schemes are available for doing this.

By locating an ultrasonic generator in a closed chamber, a standing wave pattern with peaks and nodes, is established. If a node occurs at the position of a leak or weak spot, no ultrasonic energy will escape and the defect will not be detected.

In certain instances, e.g. in detecting the malfunction of bearings, an ultrasonic detector is mechanically coupled to the casing of the bearings so that the vibrations caused by the malfunction can be mechanically transmitted to it. With such an arrangement the frequency is not set by an ultrasonic generator, but is created by the mechanical vibration itself. In such a case the ultrasonic detector circuit must be capable of sweeping over a band of frequencies to locate the one that is characteristic of the malfunction. This is usually accomplished by a heterodyning circuit which can be tuned to various frequencies, much in the manner of a radio receiver.

Ultrasonic transducers generally produce a low voltage output in response to received ultrasonic energy. Means have been proposed for increasing this output. For example, in U.S. Pat. No. 3,374,663 to Morris it is suggested that an increase in the voltage output can be achieved by serially arranging two transducers. It has been found, however, that with such an arrangement a typical transistor preamplifier loads the transducers to such an extent that the gains achieved by stacking them serially are lost. The Morris patent proposes the use of a triple Darlington configuration in order to produce a sufficiently high input impedance to prevent this degradation in the signal produced by the stack of transducers. Unfortunately, the transducers in this arrangement are not placed so that they both readily receive ultrasonic energy. Thus the Morris arrangement is not entirely satisfactory.

SUMMARY OF THE INVENTION

The present invention is directed to providing improved methods and apparatus for detecting leaks and mechanical faults by ultrasonic means. This object is achieved by using an ultrasonic generator which has a variable frequency output and by using an ultrasonic detector which includes a series stack of transducers driving a field-effect transistor preamplifier. In addition, means are provided for frequency shifting the received signal into the audio band through the use of an amplitude modulated, suppressed carrier heterodyning device.

In an illustrative embodiment of the invention the ultrasonic frequency generator typically includes a transducer crystal set for the frequency of interest. This crystal is in the feedback loop of an amplifier which drives it such that oscillations at the resonant frequency of the crystal are established. The frequency is varied about the selected frequency so as to avoid standing wave nodes at the location of a leak. This is accomplished by applying a ramp signal to the biasing network of the active element in the oscillator. This ramp signal is generated by a conventional RC circuit which has an LED flasher circuit connected across the capacitor element of that circuit.

The detector arrangement used with the present invention preferably has more than one transducer connected in series and spacially aligned in one plane such that each transducer receives the energy generated. To avoid degradation of the signal from this arrangement due to loading from the preamplifier, a field-effect transistor is used as the input to the preamplifier. When a particular frequency is expected from an ultrasonic generator, a tank circuit can be located at the input to the field-effect transistor to intensify that signal and to eliminate signals which differ therefrom.

The shift of the ultrasonic frequency into the audible range, so that a user may hear it or a meter may display it, can be accomplished with an integrated circuit function generator arranged to provide AM suppressed carrier operation. When such an integrated circuit is biased to the middle of its range, the carrier signal it is intended to produce, i.e. a signal slightly different than the received ultrasonic signal, will be suppressed. By adding the ultrasonic signal to the biasing level for this circuit the output will be only the sum and difference signals between the ultrasonic input and the carrier generated by the circuit. The sum signal is filtered out and the difference signal is used to drive headphones with which one can listen for leaks, or a meter by which to indicate them. The bias for establishing the suppressed carrier operation is under the control of a feedback loop which senses when carrier signal is present in the output signal, integrates the sensed carrier signal over a period of time to arrive at an average value, and uses the average value to vary the bias such that the carrier signal is eliminated.

In a preferred embodiment of the method according to the present invention, leaks are detected not only by the passage of frequency-shifting ultrasonic energy through a hole in a container, but also by the sound made by the bursting of bubbles created by a liquid which is applied over the surface of the container after it is pressurized. This liquid has a surface tension which causes the formation and the bursting of the bubbles when they are at a size which produces ultrasonic energy when they burst, which energy is readily detected by the circuitry.

BRIEF DESCRIPTION OF THE DRAWINGS

The foregoing and other features of the present invention will be more readily apparent from the following detailed description and drawings of an illustrated embodiment of the invention in which:

FIG. 1 is a diagram illustrating the overall circuit arrangement for the present invention and its use in connection with the detection of a leak;

FIG. 2 is a schematic diagram of the ultrasonic generator shown in FIG. 1; and

FIG. 3 is a schematic diagram of the transducer and preamplifier shown in FIG. 1.

DESCRIPTION OF AN EXEMPLARY EMBODIMENT

FIG. 1 represents a block diagram of an apparatus and method for ultrasonically detecting mechanical faults, for example bearing failures and leaks in containers. By way of example, a container 10 is illustrated. Located within the container is an ultrasonic generator 12 which produces ultrasonic sound waves in the vicinity of, e.g., 40 KHz. According to the present invention this generator produces an output which is frequency modulated about its 40 KHz center frequency at a much lower frequency, for example 5-20 Hz. By means of this variation in the output of the generator, the standing wave pattern created within the container varies such that the standing wave nodes do not remain constant at one position.

At position 10' there is a small hole in the container 10 from which ultrasonic energy may escape and be detected by an ultrasonic transducer 14. The output of the transducer 14 is applied to a field-effect transistor preamplifier 16 whose gain is under the control of sensitivity control 16', which varies the supply voltage to the preamplifier as shown in FIG. 3.

From the preamplifier 16 the ultrasonic signal is delivered to a transistor driver amplifier 20 which amplifies it again and in turn capacitively couples it to the input (pin 1) of a function generator 22 via capacitors 29, 29'. The generator 22 acts to frequency shift the amplified ultrasonic signal into the audible frequency range. This audio signal from the output (pin 2) of circuit 22 is applied to a headphone transistor amplifier 24 which may include a Darlington transistor arrangement as indicated by the letter D on the drawing. From the amplifier 24 it passes via a filter and transformer 25 to a set of headphones 26. The filter acts to eliminate the carrier and any extraneous frequencies, e.g. the sum signal, from the signal applied to the headphones. Circuit 22 also has its output applied through a transistor driver amplifier 23 to a frequency-compensated meter amplifier circuit 35. Filter elements in circuit 35 also act to cancel the carrier signal and any extraneous signal, leaving only the audio signal. Following the amplifier 35 there is a temperature compensation circuit 36 and a meter signal conditioning circuit 37 whose output is applied to a meter 38. Circuit 37 acts to put the signal in proper condition for display by the meter 38.

Temperature compensation circuit 36 includes a thermistor 36' which is part of a voltage divider network leading to the meter signal condition circuit 37. As a result, an increase in temperature will cause the proportion of voltage applied to the meter circuit to be changed in such a way as to compensate for the change in gains due to the temperature increase.

In meter signal condition circuit 37 there are two diodes, one in the form of a germanium transistor 39 which is wired as a diode. The effect of this diode is to rectify the AC signal received so as to generate a DC signal for application to the meter. This DC signal is ordinarily applied through resistor 37' to the meter. When the meter is to be operated in a logarithmic mode, a switch 37" is closed, placing a diode 39' and resistor 37''' across resistor 37'. Resistor 37''' is significantly smaller than resistor 37' and thus changes the scale for the meter. In addition the diode 39' in series with resistor 37''' acts to crete a voltage threshold which eliminates noise in the circuit when it is in the more sensitive logarithmic scale.

As a result of the arrangement of FIG. 1, ultrasonic signals leaking from container 10 are picked up by transducer 14, amplified and frequency shifted so that a user will have an indication of the existence of a leak through the sound heard in headphones 26 and level displayed on meter 38.

The actual frequency shift of the ultrasonic signal is accomplished in function generator 22. This generator may be a commercially-available integrated circuit, such as the EXAR 2206, which has been wired to produce sine wave outputs at a frequency determined by tuning resistor 30 connected to pin 7 of the circuit as well as capacitor 22' connected between pins 5 and 6. One characteristic of this circuit is that a particular bias applied to its input (pin 1) will cause it to produce an amplitude-modulated (AM), suppressed-carrier output. The bias to obtain this suppressed-carrier modulation is derived from variable resistor 28. If capacitor 22' and resistor 30 are selected to produce a carrier signal that differs from the ultrasonic signal by a frequency in the audio band, the output of circuit 22 will be an audio signal related to the input ultrasonic signal and a much higher signal. In particular the output signal will be equivalent to the sum and difference frequencies of the ultrasonic signal and the carrier signal generated by circuit 22, but the carrier signal itself will not be present in the output. If, for example, resistance 30 is set so that circuit 22 generates a 42 KHz signal and the ultrasonic signal applied through capacitors 29 and 29' to circuit 22 is at 40 KHz, the output will be at 2 KHz and at 82 KHz. Since only the audio band signal is desired, filter circuits 25 and 35 are designed to eliminate the 82 KHz sum signal.

Although a proper bias on the input to circuit 22 will eliminate or suppress the carrier generated by that circuit, it has been found that this adjustment is critical and some carrier may leak through due to temperature and voltage variations. Also as the carrier frequency is changed due to changes in the setting of resistor 30 there are changes in the circuit operation that may cause the carrier to appear in the output unless there is an adjustment of the bias. In order to provide this adjustment a servo or feedback network is provided. In particular the output of circuit 22 (pin 2) is applied through driver circuit 23 to a highpass filter 26 which passes only frequencies above 20 KHz. The output of filter 26 is applied to a Darlington transistor arrangement that forms amplifier 27. Amplifier 27 acts to amplify and integrate or average, via capacitor 27', the carrier signal received. This signal is also inverted in the amplifier so as to vary the bias from resistor 28 in such a way as to correct for the presence of the carrier in the output signal. Although some carrier may always exist, sufficient to create an error signal, this level will be low enough to avoid erroneous indications in the earphones 26 and the meter 38.

In one embodiment of the present invention the transducer is used to detect vibrations, for example from bearings, through a direct mechanical connection between the noise source, e.g., the bearing housings, and the transducer crystals. In such a case the bandwidth of signals detected may range from 20 KHz to 100 KHz, and particular bands of this frequency range may be selected by changing the position of variable resistor 30 so as to create a carrier frequency in circuit 22 which moves over this range.

In another embodiment the transducer is located in space at some distance from a hole in a container that has 40 KHz generator 12 within it. In such a case the preferred 40 KHz mode of operation of the detector is used.

When operating in this acoustic pick-up mode where the transducer is held in space, the main tuning resistance 30 is rotated to a detent at one end. Near this detent the resistance of main turning resistor 30 drops to near zero. Upon entering the detent, a switch 34 changes position, thereby connecting preset resistor 32 into the frequency control line for circuit 22 and enabling a 40 KHz resonant filter 21. The resonant filter 21 acts to boost frequencies in the 40 KHz range and to eliminate those substantially outside this band of frequencies. Resistor 32 acts to set the frequency of circuit 22 at some value in the vicinity of 40 KHz, e.g. 42 KHz.

Power for the circuit of FIG. 1 is created by a battery 40 which is applied through power switch 50 to a DC-to-DC converter 42 that generates a 15 volt output applied to the various parts of the circuit. Positioned across the battery input to the DC-to-DC converter is a recharging indicator circuit which includes elements 44–47. When the power switch 50 is closed, the voltage from battery 40 applies bias to transistors 45 and 47, which are Darlington transistor arrangements. Variable resistor 44 is set such that transistor 47 is turned on, thereby turning transistor 45 off. When the battery voltage drops, however, the bias on the base of transistor 47 becomes insufficient to cause it to remain in the conduction state. As it turns off, it causes transistor 45 to turn on, which causes current to be drawn through light emitting diode 46. This diode indicates when the battery must be recharged. It has been found that through the use of cascaded arrangements of Darlington transistors, such as transistors 45 and 47, the circuit has a sharp response so that a particular level of degradation in the amplitude of the battery voltage can be set by variable resistance 47 and it will be accurately indicated.

Now that the details of the receiver and frequency conversion circuits have been described, reference will be made to the ultrasonic generator 12, the details of which are shown in FIG. 2. This generator is typically set to produce an output ultrasonic signal at approximately 40 KHz. To accomplish this a 40 KHz crystal transducer 114, such as that made by Panasonic Corp., is employed in the feedback circuit of an oscillator which includes transistor 110. When the circuit is turned on, current initially flows from the power supply through an amplitude control resistance 118 and the primary of a step-up transformer 112 to transistor 110. This creates a voltage level across the crystal transducer 114 which will begin to resonate at its fundamental frequency of 40 KHz. The resonant frequency from transducer 114 is passed to the base of transistor 110 through a filter network comprising capacitor 115, a parallel combination 116 of a capacitor and resistor, and capacitor 117. This filter network passes signals in the 40 KHz range and eliminates harmonics. Inversion of the feedback signal in order to have the positive feedback needed for oscillation is by means of the wiring of the secondary of transformer 112 which is connected across transducer 114. With this arrangement the crystal will be driven at its resonant frequency of 40 KHz and will produce an ultrasonic wave at that frequency.

If the generator is located within a container, such as container 10 shown in FIG. 1, the ultrasonic energy produced by the crystal will fill the container and will leak out of the container at openings, such as hole 10'. When in a container, however, a constant output from transducer 114 will result in the establishment of standing waves in the container. Thus it is possible that a null of the standing wave will occur at the position of the leak 10', which would result in failure to detect the leak. To compensate for this, generator 12 causes the standing wave pattern to vary slowly by varying its output frequency. This is accomplished by means of resistor 120, capacitor 122 and flasher light-emitting diode 24, e.g., a Litronix Flasher Mod. FRL-4403. With this arrangement current flows through resistor 120 and charges up capacitor 122. As it charges it changes the bias on transistor 110, which results in a frequency shift in the oscillator of perhaps 2–5 KHz. When the breakdown voltage of the flasher 124 is reached it will discharge the voltage across capacitor 122 and the process will repeat. Typically the resistance 120 and capacitor 122 are selected so that the variation in frequency occurs at a sub-audio rate, e.g. 5–20 Hz. However, any convenient frequency variation can be selected.

The circuit of FIG. 2 can be altered by replacing the flasher LED with some other type of voltage breakdown device. Also, the secondary of transformer 112 can be wired as shown in FIG. 2 so there is no voltage step-up. This arrangement lowers the impedance across the crystal, thereby lowering its Q and increasing the frequency variation achieved.

By varying the frequency output at a slow rate, not only is the problem of node points avoided, it is psychologically easier for a listener to detect leaks. In addition the receiver circuit could be modified so as to respond only to this varying frequency, thus making it more sensitive and improving its signal-to-noise ratio.

The transducer and preamplifier which detect the signal produced by the generator of FIG. 2 are shown in the schematic of FIG. 3. In FIG. 3 a group of series-connected ultrasonic transducers are shown for receiving ultrasonic energy and converting it into electrical energy. Each transducer may be a 40 KHz piezoelectric crystal, such as those manufactured by Panasonic Corporation. While three such crystals are shown in FIG. 3, the number of such crystals is not critical and two, or more than three, may be employed. By arranging these transducers adjacent to each other in one plane, each receives acoustic energy and the electrical signals created thereby are added because of the series connection, thereby giving a larger output than when a single transducer is used. The effectiveness of such an arrangement of transducers could be reduced if the impedance of the preamplifier is low. To avoid this a field-effect transistor preamplifier is used with an input stage field-effect transistor 220. The output of this transistor is applied through capacitor 222 to field-effect transistor 230. The drain of transistor 230 is the output of the preamplifier that is connected to driver circuit 20 shown in FIG. 1. As explained previously, the receiver can be used in a mode which allows it to scan ultrasonic frequencies from 20 KHz to 100 KHz or it can be used in a preferred 40 KHz band. When used in the preferred 40 KHz band, capacitors 212 and 214 as well as inductance 216, are used to create a resonant circuit with a frequency response centered about 40 KHz. This will increase the size of the voltage at 40 KHz up to 40 times and will greatly attenuate frequencies removed from this center band. When this resonant circuit is used it is important that transistor 220 be a MOSFET.

The gain of the preamplifier is controlled by variable resistance 16' shown in FIG. 1. The voltage derived from the variable resistance is applied to the drains of transistors 220, 230 through respective resistances. Because the output level is achieved in this manner, i.e. with the amplitude control being outside the signal path, any scratchiness in resistor 16' will not be heard in the microphones 38. In addition, any overload in the preamplifier is easily compensated by reducing the voltage level to the circuit.

The transducers 210, regardless of how many are used, are serially-wired together and are spaced close together, preferably in a flat plane. Having these transducers arranged next to each other on a flat plane effectively focuses the overall transducer at infinity. If desired, the transducers could be located on a curved or parabolic surface such that they would be focused to receive energy originating from a source at any distance closer than infinity. However, in most cases this is not necessary.

Referring once more to FIG. 1 the detection of a leak 10' can also be achieved without an ultrasonic source if the container is pressurized and its interior surface is covered with a liquid having a particular range of surface tension. In such a case the liquid is caused to form small bubbles by the passage of the pressurized gas through the leak, which bubbles break and reform when they have obtained a diameter of from 0.005 to 0.02 inches. Breaking of bubbles of this size produces ultrasonic energy that can be detected by the transducer of circuit 14. If the liquid has too low a surface tension, e.g. water, then the bubbles will not form and no improvement in results will be achieved. On the other hand, if the surface tension is too great, such as that for a viscous soap, the bubbles grow too large for ultrasonic energy generation when they burst and the rate of generation is too slow. Therefore, a balanced surface tension between these extremes is necessary. However, suitable liquids can easily be found with this characteristic by experimentation. One liquid which has been found to be particularly useful consists of a 4% aqueous solution of sodium (2) ethyl hexyle sulfate, i.e., $C_4H_9CH(C_2H_5)CH_2SO_4Na$. With this liquid the popping noise created by the forming and bursting of the bubbles in an excellent indicator of the existance of a leak. This liquid has a surface tension at 25° C. of 63 dynes per centimeter. Water has a surface tension of about 23 dynes/cm. Thus liquids with surface tension in the range of 50-70 dynes/cm are preferable.

With this liquid small leaks which cannot be detected will produce bubbles. When these bubbles break, however, they do produce ultrasonic energy which can be detected.

While the present invention has been particularly shown and described with reference to a preferred embodiment thereof, it will be understood by those skilled in the art that various changes in form and details may be made therein without departing from the spirit and scope of the invention.

What is claimed is:

1. Apparatus for indicating the presence of ultrasonic energy comprising:

an ultrasonic transducer means for converting ultrasonic energy into electrical energy having a related ultrasonic frequency;

an amplifier means for amplifying the electrical energy produced by said transducer means to produce an amplified ultrasonic signal;

a heterodyne means for translating the frequency of the amplified ultrasonic signal into the audio frequency range by modulating it with a carrier frequency signal whose frequency differs from the ultrasonic frequency by a frequency within the audio range, said heterodyne means including a carrier frequency signal generator and a suppressed-carrier amplitude modulator means for modulating said amplified ultrasonic signal with said carrier signal to produce an output audio frequency signal related to the amplified ultrasonic signal; and an indicator means responsive to the amplitude of the audio frequency signal for indicating an output level related to the level of the ultrasonic energy.

2. Apparatus as claimed in claim 1 wherein said apparatus is adapted to indicate ultrasonic energy having a wide range of ultrasonic frequencies, said carrier frequency signal generator being adjustable to change said carrier frequency signal so that the ultrasonic energy at different parts of its range of frequencies is indicated.

3. Apparatus as claimed in claim 1 wherein said ultrasonic transducer means comprises at least two piezoelectric crystals electrically connected in series and spaced adjacent each other on a generally planar surface such that they are both exposed to said ultrasonic energy, the degree of curvature of said planar surface being related to the distance from said surface for which said transducer means is focused to receive ultrasonic energy.

4. Apparatus as claimed in claim 3 wherein the ultrasonic transducer means comprises three crystals positioned adjacent each other on a flat planar surface.

5. Apparatus as claimed in claim 3 wherein said amplifier means comprises an input field-effect transistor, said crystals being connected in series between a gate terminal of said field-effect transistor and a common reference level, said input field-effect transistor being biased to have a high impedance between the gate terminal and the common reference level sufficient to avoid loading the series arrangement of crystals.

6. Apparatus as claimed in claim 5 wherein said amplifier means further includes a second field-effect transistor connected as an amplifier, said input field-effect transistor also being connected as an amplifier and supplying its output to the input of the amplifier formed by the second field-effect transistor.

7. Apparatus as claim in claim 1 wherein said apparatus is adapted to indicate ultrasonic energy in a narrow band of ultrasonic frequencies, said amplifier means includes a resonant circuit at its input which is tuned to the center of the narrow band of frequencies, and said carrier frequency signal generator produces a carrier frequency signal at one frequency which differs from the narrow band of ultrasonic energy frequencies by a frequency within the audio range.

8. Apparatus as claimed in claim 1 wherein the amplification produced by said amplifier means is variable by varying a power supply voltage level applied to said amplifier means and used to operate it.

9. Apparatus as claimed in claim 1 wherein said heterodyne means includes a feedback means for assuring suppressed carrier operation of said modulator means by feeding part of the modulator output signal back to the modulator.

10. Apparatus as claimed in claim 9 wherein said modulator means produces suppressed carrier operation when a particular bias voltage is applied to it and said heterodyne means further includes variable bias voltage source means for supplying the bias voltage to said modulator, said feedback means comprising filter means for blocking the audio frequency signal and passing the carrier frequency signal if present, said filter means receiving the output of said modulator, means for averaging the carrier frequency output of said filter means over a period of time to produce an error signal, and means for applying the error signal to the variable bias voltage source so as to change the output bias voltage in such a way as to eliminate the carrier signal in the output of the modulator.

11. Apparatus as claimed in claim 1 wherein said indicator means includes means for converting the audio frequency signal into sound waves, the amplitude of which are a measure of the ultrasonic energy.

12. Apparatus as claimed in claims 1 or 11 whereing said indicator means includes a meter and means for converting the audio frequency signal into a signal suitable for display by said meter.

13. Apparatus as claimed in claim 1 further including a battery having an output voltage, a voltage level generator operated from the output voltage of said battery for supplying voltage to said apparatus, and a recharge indicator means for indicating when the output voltage of said battery is below a predetermined level.

14. Apparatus as claimed in claim 13 wherein said rechange indicator means comprises a first Darlington transistor arrangement connected as a first amplifier, means for applying a portion of the battery output voltage to the input of the first amplifier, a second Darlington transistor arrangement connected as a second amplifier, said second amplifier receiving the signal amplified by the first amplifier, and a light-emitting diode connected to the output of said second amplifier such that when the portion of the output voltage falls below the predetermined level the first Darlington transistor arrangement stops conducting current, causing the second Darlington transistor arrangement to draw current through the light-emitting diode.

15. Apparatus as claimed in claim 7 wherein said ultrasonic energy is created by an ultrasonic generator, said generator comprising:

an oscillator circuit means for producing an electrical oscillation in the narrow ultrasonic band of frequencies, said oscillator means including a feedback path that includes a piezoelectric crystal, said crystal having a resonant frequency in said narrow band of frequencies and converting the electrical oscillation signals in the feedback path into ultrasonic energy; and sweep means for causing the output of said oscillator to vary within said narrow band of frequencies at a periodic frequency rate that is no higher than the upper limit of the audio range.

16. Apparatus as claimed in claim 15 wherein said oscillator circuit means is a transistor oscillator with at least one transistor and said sweep means is a means for periodically varying the bias applied to said transistor.

17. Apparatus as claimed in claim 16 wherein said sweep means comprises a capacitance charged from a voltage source through a resistance, and a threshold voltage level conduction device connected across said capacitance, said conduction device having a low impedance when the voltage across it is greater than a particular level and a high impedance when the voltage is below the particular level, the values of the resistance, capacitance and particular level being related so that the bias voltage builds up from a first level to a second level at one rate and then returns to the first level at a different rate when the particular level is exceeded and the capacitance is discharged through the conduction device, said buildup and return occurring at the periodic frequency rate.

18. Apparatus as claimed in claims 15 or 16 wherein the periodic frequency rate is in the range from 5 to 20 Hz.

19. In a method of detecting small openings or thin spots in an otherwise closed container, involving the steps of positioning a source of ultrasonic energy within said container, detecting the existence of ultrasonic energy outside the container with an ultrasonic detector that converts ultrasonic energy into energy in the audio range, and locating the origin of the ultrasonic energy outside the container by passing the ultrasonic detector over the outer surface of the container to locate the position at which the largest audio energy signal is obtained, the improvement comprising the step of sweeping the frequencies of the ultrasonic source over a band of frequencies at a rate below the upper limit of the audio range so that no standing wave node continuously exists at one location on the surface of the container.

20. The method of claim 19 further including the steps of pressurizing the container with a gas, and covering the outer surface of the container with a layer of a liquid having a surface tension such that the pressurized gas passing through small openings in the container causes the formation and bursting of bubbles in the layer of liquid at that location, said bubbles being of a size to generate ultrasonic energy when they burst.

21. The method of claim 19 wherein the sweep frequency of the ultrasonic source is in the range of 5 to 20 Hz.

22. In a method of detecting small openings in an otherwise closed container, involving the steps of pressurizing the container with a gas, detecting the existence of ultrasonic energy outside the container due to the pressure of the gas through the opening with an ultrasonic detector that converts the ultrasonic energy into energy in the audio range, and locating the origin of the ultrasonic energy outside the container by passing the ultrasonic detector over the outer surface of the container to locate the position at with the largest audio energy signal is obtained, the improvement comprising the step of covering the outer surface of the container with a layer of a liquid having a surface tension such that the pressure of the gas through small openings in the container causes the formation and bursting of bubbles in the layer of liquid at that location, said bubbles having a size such that their bursting generates ultrasonic energy.

23. The method of claims 20 or 22 wherein the liquid has a surface tension in the range of 50 to 70 dynes/cm. and the bubbles have a diameter in the range of 0.005 to 0.02 inches.

24. The method of claim 23 wherein the liquid is a 4% aqueous solution of sodium (2) ethyl hexyle sulfate.

25. An ultrasonic energy generator comprising:
an oscillator circuit means for producing an electrical oscillation in a narrow ultrasonic band of frequencies, said oscillator circuit including a feedback path with a piezoelectric crystal, said crystal having a resonant frequency in said narrow band of frequencies and converting the electrical oscillation signals in the feedback path into ultrasonic energy; and
sweep means for causing the output of said oscillator to vary within said narrow band of frequencies at a periodic frequency rate that is no higher than the upper limit of the audio range.

26. Apparatus as claimed in claim 25 wherein said oscillator circuit means is a transistor oscillator with at least one transistor and said sweep means is a means for periodically varying the bias applied to said transistor.

27. Apparatus as claimed in claim 26 wherein said sweep means comprises a capacitance charged from a voltage source through a resistance, and a threshold voltage level conduction device connected across said capacitance, said conduction device having a low impedance when the voltage across it is greater than a particular level and a high impedance when the voltage is below the particular level, the valves of the resistance, capacitance and particular level being related so that the bias voltage builds up from a first level to a second level at one rate and then returns to the first level at a different rate when the particular evel is exceeded and the capacitance is discharged through the conduction device, said buildup and return occurring at the periodic frequency rate.

28. Apparatus as claimed in claim 25 wherein the periodic frequency rate is in the range from 5 to 20 Hz.

29. An ultrasonic transducer for converting ultrasonic energy into electrical energy having a selected ultrasonic frequency comprising:
at least two piezoelectric crystals electrically connected in series and spaced adjacent each other on a generally planar surface such that both are exposed to the ultrasonic energy, the degree of curvature of said planar surface being related to the distance from said surface for which said transistor means is focused to received ultrasonic energy; and
an amplifier means including an input field-effect transistor, said crystals being connected in series between a gate terminal of said field-effect transistor and a common reference level, said input field-effect transistor being biased to have a high impedance between the gate terminal and the common reference level sufficient to avoid loading the series arrangement of crystals.

30. Apparatus as claimed in claim 29 wherein said amplifier means further includes a second field-effect transistor connected as an amplifier, said input field-effect transistor also being connected as an amplifier and supplying its output to the input of the amplifier formed by the second field-effect transistor.

31. Apparatus as claimed in claims 29 or 30 wherein the amplification produced by said amplifier means is variable by varying a power supply voltage level applied to said amplifier means and used to operate it.

* * * * *